United States Patent [19]

Djuric et al.

[11] Patent Number: 4,971,997
[45] Date of Patent: Nov. 20, 1990

[54] FURYL, PHENYLENE, AND THIENYL LEUKOTRIENE B₄ ANALOGUES

[75] Inventors: Stevan W. Djuric, Glenview; Richard A. Haack, Chicago; Stella S. Yu, Morton Grove, all of Ill.

[73] Assignee: G. D. Searle & Co., Chicago, Ill.

[21] Appl. No.: 390,567

[22] Filed: Aug. 7, 1989

Related U.S. Application Data

[60] Division of Ser. No. 158,454, Feb. 18, 1988, Pat. No. 4,855,324, which is a continuation-in-part of Ser. No. 130,355, Dec. 8, 1987, abandoned.

[51] Int. Cl.⁵ .................. A61K 31/165; C07C 233/00
[52] U.S. Cl. ................................... 514/621; 514/622; 564/169; 564/170
[58] Field of Search ............... 564/169, 170; 514/621, 514/622

[56] References Cited

U.S. PATENT DOCUMENTS 4,546,194 10/1985 Miyano .
4,732,901 3/1988 Buckle .
4,855,324 8/1989 Djuric et al. ..................... 514/570

OTHER PUBLICATIONS

Biochem and Biophys. Res. Comm., 138, 540–546 (1986).
Lewis et al., J. Clin. Inves., 73, 889–897 (1984).
Bray, Brit. Medical Bull., 39, 249–254 (1983).
Furber et al., J. Chem. Soc., Perkin Trans I, 7, 1573 (1987).
Chem. Abstracts No. 84-271464/44.
Derwent No. 85-249007/40.
Derwent No. 85-249005/40.

Primary Examiner—Alan Siegel
Attorney, Agent, or Firm—Paul D. Matukaitis; Roger A. Williams

[57] ABSTRACT

This invention relates to a compound of the formula:

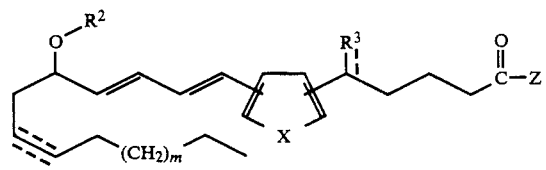

or a pharmaceutically acceptable salt thereof
wherein X is oxygen, sulfur, or —CH=CH—;
wherein Z is $OR^1$ or —$NR^4R^5$;
wherein $R^1$ is hydrogen, lower alkyl, or a pharmaceutically acceptable cation;
wherein $R^2$ is H, —$CH_3$ or —$C_2H_5$;
wherein $R^3$ is OH, H or =O;
wherein $R^4$ and $R^5$ may independently be hydrogen, or lower alkyl having 1–6 carbon atoms, or $R^4$ and $R^5$ may act together with N to form a cyclic amide of the formula:

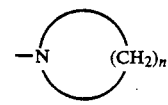

wherein n is an integer from 4–5; and m is an integer from 0–4.

More particularly, this invention relates to compounds of the above formula which have utility as $LTB_4$ antagonists.

6 Claims, No Drawings

FURYL, PHENYLENE, AND THIENYL LEUKOTRIENE B4 ANALOGUES

This application is a division of U.S. Ser. No. 07/158,454 filed Feb. 18, 1988 now U.S. Pat. No. 4,855,324 which is a continuation-in-part of U.S. Pat. Ser. No. 07/130,355 filed Dec. 8, 1987, now abandoned.

BACKGROUND OF THE INVENTION

1. Field of the Invention

The present invention relates to pharmaceutical agents (compounds) which act as leukotriene B4 (LTB4) antagonists in mammals. The compounds of the present invention are useful in treating inflammatory conditions in mammals such as psoriasis. Crohn's disease, ulcerative colitis and the like.

(b) Prior Art

LTB4 (Formula I) is an arachidonic acid metabolite which is produced by the 5-lipoxygenase pathway. Pharmacologically, LTB4 is an important mediator of inflammation in mammals. As a mediator of inflammation, LTB4 is known to induce chemotaxis, chemokinesis, aggregation, and degranulation of leukocytes in vitro, and to induce accumulation of polymorphonuclear leukocytes, and increase vascular permeability and edema formation in vivo.

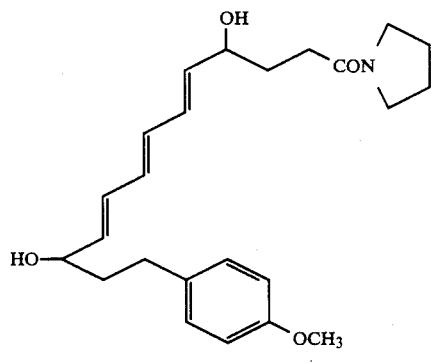

Particularly high levels of LTB4 are detected in lesions in inflammatory diseases such as rheumatoid or spondylarthritis, gout, psoriasis, ulcerative colitis, Crohn's disease and some respiratory diseases.

Accordingly, it is an object of this invention to produce compounds for use as pharmaceutical agents which will exhibit LTB4 antagonist activity in mammals.

A potential LTB4 antagonist (Formula II), which is structurally different from the compounds of the present invention, is disclosed in Biochem. and Biophys. Res. Comm., 138 540–546 (1986).

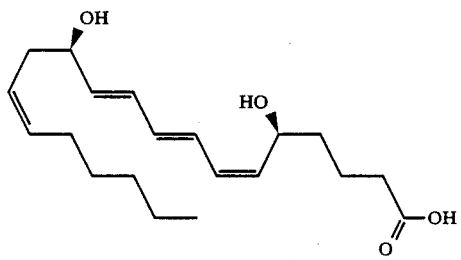

In this article, the authors also suggest that they have found antagonistic activity in a series of unidentified unsaturated dihydroxy fatty acid derivatives which are to be the subject of a future publication.

Furber, et al., disclose the preparation of LTB4 analogues of Formulas III-V wherein phenyl or pyridyl ring provides the trans, trans double bonds corresponding to C-8 and C-10 trans trans double bonds in naturally occurring LTB4. J. Chem. Soc. Perkin Trans. I, 7 1573 (1987).

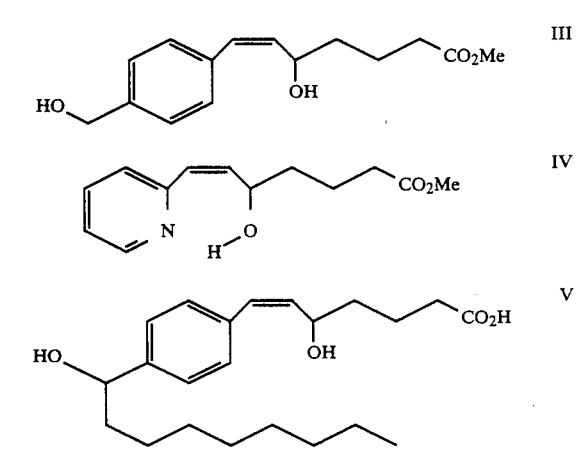

The pharmacology of the biologically active leukotrienes is generally discussed in J. Clin. Invest. 73, 889-897 (1984).

SUMMARY OF THE INVENTION

This invention relates to a compound of the formula:

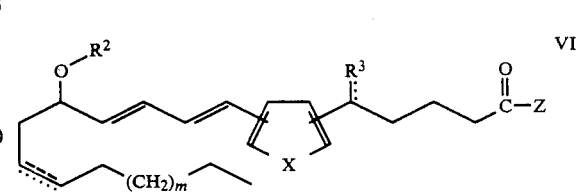

or a pharmaceutically acceptable salt thereof
wherein X is oxygen, sulfur, or —CH=CH—;
wherein Z is $OR^1$ or —$NR^4R^5$;
wherein $R^1$ is hydrogen, lower alkyl, or a pharmaceutically acceptable cation;
wherein $R^2$ is —H, —$CH_3$ or —$C_2H_5$;
wherein $R^3$ is OH, H or =O;
wherein $R^4$ and $R^5$ may independently be hydrogen, or lower alkyl having 1-6 carbon atoms, or $R^4$ add $R^5$ may act together with N to form a cyclic amide of the formula:

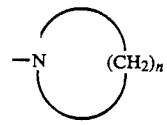

wherein n is an integer from 4-5; and
wherein m is an integer from 0-4.

DETAILED DESCRIPTION

This invention encompasses compounds of Formula VI as previously described. A particularly preferred embodiment of the present invention is encompassed by a compound of the formula:

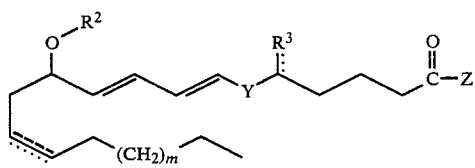

or a pharmaceutically acceptable salt thereof.
wherein Y is

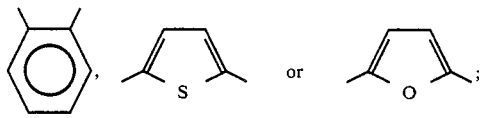

and wherein $R^3$, $R^4$, $R^5$, n, m, and Z are as previously defined for Formula VI.

The term "lower alkyl" as used to described $R^1$, $R^4$, and $R^5$ means straight or branched chain alkyls having 1–6 carbon atoms.

The term "pharmaceutically acceptable cations" as used to describe $R^1$ refers to cations such as ammonium, sodium, potassium, lithium, calcium, magnesium, ferrous, zinc, copper, manganous, aluminum, ferric, manganic, ammonium, tetraalkyl-ammonium, and the like.

The term "pharmaceutically acceptable non-toxic addition salts" refers either to those base derived salts of any compound herein having a carboxylic acid function.

The base derived salts may be derived from pharmaceutically acceptable non-toxic inorganic or organic bases. Among the inorganic bases employed to produce said pharmaceutically acceptable salts are the hydroxide bases of the "pharmaceutically acceptable cations" disclosed above.

Among the organic bases employed to produce said pharmaceutically acceptable salts are the pharmaceutically acceptable non-toxic bases of primary, secondary, and tertiary amines Especially preferred non-toxic bases are isopropylamine, diethylamine, ethanolamine, dicyclohexylamine, choline, and caffeine.

All the pharmaceutically acceptable non-toxic addition salts are prepared by conventional processes well known to those of ordinary skill in the art.

The compounds of this invention are generally prepared according to the scheme set out in Charts A–C, wherein two side chains are substituted onto a dihalo aromatic moiety. By dihalo is meant dibromo, bromoiodo or diiodo. In Charts A–C, the halo group is represented by the letter "Q". By aromatic moiety is meant phenyl. thienyl or furyl, corresponding to "X" in the aryl ring being —CH═CH—, —S—, and —O—respectively.

As disclosed in Chart A, the first chain can be added to the aromatic moiety of formula (X) by performing a nucleophilic substitution of one of the halogens "Q" such as via a reaction with 4-pentynoic acid, CuI, and $Pd^o$ in a basic solvent such as diethyl amine. In aromatic moieties having both a bromo and an iodo substituent, the substitution of the pentynoic acid occurs preferentially at the iodo bearing carbon atom to produce a 5-aryl-4-pentynoic acid species (XI).

Hydration of the triple bond, such as by concentrated sulfuric acid, produces a keto group at the C-5 position of the pentynoic acid, i.e., a 5-aryl-5-oxopentanoic acid (XII). The carboxylic acid of XII is rendered neutral by esterification, such as by reaction with diazomethane, to produce the corresonding methyl ester (XIII).

The second side chain is optionally 11 to 15 carbons long. Preferably, its length is selected to provide a 20 carbon chain length corresponding to the length of naturally occurring $LTB_4$ (I). Thus, when the first and second side chains on the aromatic moiety are ortho to each other, the first side chain provides 5 carbon atoms whereas the aromatic moiety provides only 2 carbon atoms (having a 6-cis double bond) to the chain. Accordingly, the remaining carbon atoms are provided by the second side chain which is preferably 13 carbons long,. i.e. $20 - 7 = 13$ carbons. When the second side chain is 13 carbon atoms long, m of Formula VI is 2. Analagously, when the first and second side chains are para to each other, the aromatic moiety provides 4 carbon atoms to the chain and the second side chain is preferably 11 carbons long (m of Formula VI is 0).

The second side chain may optionally have an unsaturated site so as to provide unsaturation at the C-13 position in the backbone of the $LTB_4$ analogues, which correspond to the C-13 cis-double bond in naturally occurring $LTB_4$. By "unsaturation" as used herein is meant an individual double or triple bond. Examples of unsaturated acyl chlorides corresponding to Formula XX of Chart B are given in Examples 30 and 31.

The addition of the second side chain to the aromatic moiety is preferably accomplished using two segments. The first segment is preferably short and will have two reactive terminus, both of which are preferably nucleophilic. Substitution of this segment onto the monohaloaromatic moiety XIII to produce XV is accomplished by performing a nucleophilic substitution at the carbon bearing the second bromo or iodo group, preferably with the nucleophile, trans-1,2 -bis(tributylstannyl)ethylene XIV, in the presence of a catalyst, such as $Pd^o$ in nonpolar solvent, such as toluene, and in the presence of heat. The nucleophile XIV is prepared according to the procedure of Corey et al., J. Org. Chem. 40, 3788 (1975).

The tri-(n-butyl)stannyl terminus of XV is converted to the corresponding trans vinyl bromide XVI by reaction with elemental bromine in $CCl_4$ at low temperature, preferably around $-20°$ C.

The second and longer segment of the second side chain is selectively substituted and built up to provide the remainder of the 11–13 carbon side chain and has a reactive terminus for substitution of the vinyl bromo group of XVI. For example, an acyl chloride having 7 to 9 carbon atoms is reacted at low temperature, preferably around $0°$ C., with bis-(trimethylsilyl)acetylene in the presence of $AlCl_3$ in a polar aprotic solvent, such as $CH_2Cl_2$ to produce XXI. When m of Formula VI is 2 and X in the aryl ring is —CH═CH—, the acyl chloride is nonanyl chloride and the product XXI is 1-trimethylsilyl-1-undecyn-3-one (Example 5).

The keto group in XXI is reduced to the corresponding alcohol. XXII. preferably by reaction with a metal hydride, such as $NaBH_4$. Removal of the terminal trimethylsilyl group to produce the terminal alkyne XXIII is accomplished by reaction of XXIII with 1M tetra-n-butylammonium fluoride in a polar solvent such as tetrahydrofuran.

The hydroxyl group of XXIII may optionally be protected as an ether, preferably by reaction with dihydropyran in the presence of a catalytic amount of an acid such as p-toluenesulfonic acid, producing the corresponding tetrahydropyranyl (THP) ether XXIV.

Reaction of XXIV with a trialkylstannane, preferably tri-n-butylstannane, in the presence of a catalytic amount of azoisobutyronitrile (AIBN) produces XXV, wherein a trans addition occurs across the triple bond with the bulky trialkylstannyl group adding at the terminus. The resulting compound XXV is now suitable for reaction with XVI in the presence of a Pd catalyst to form XXVI, wherein the trans character about C-1 and C-3 on the second side chain are 100% and 75% retained respectively.

Having formed the carbon skeleton for the products of this invention in XXVI, its THP ether may be cleaved by acid hydrolysis in methanol to the corresponding hydroxyl group producing the hydroxyketoester XXVII. The hydroxyketoester XXVII may be reduced to the corresponding dihydroxyester of this invention XXIX with a metal hydride, preferably $NaBH_4$ is a protic solvent such as methanol at reduced temperature.

Alternatively, the keto group of XXVI may first be treated with a metal hydride as above to produce the corresponding hydroxy-THP ether of XVII. Acid hydrolysis of the hydroxy-THP-ether of XXVIII in methanol produced not only the hydrolyzed dihydroxy ester of this invention XXIX, but it also produced the methyl ether XXX corresponding to $R^2=CH_3$ in Formulas VI and VII. When the first and second side chains are ortho to one another, the reaction of XXVIII with a catalytic amount of acid in methanol also produces a pair of benzofuran fused ring stereoisomers corresponding to Example 14 herein.

The esters of this invention, such as XXVII, XXIX, and XXX, can be converted into their corresponding carboxylate salts by basic hydrolysis with an aqueous alcoholic solution of a base having a pharmaceutically acceptable cation. The method for formation of the base salts of a carboxylic acid is well known by those of ordinary skill in the art.

In yet an alternative scheme, which achieves the necessary diversity for Z of Formulas VI and VII, the ester of XIII is converted into its corresponding amide XVII by reaction in the presence of $NH_4Cl$ with a primary or secondary amine of the formula $H-NR^4R^5$ wherein $R^4$ and $R^5$ are independently hydrogen or lower alkyl of of 1-6 carbon atoms or $R^4$, and $R^5$ may act together with N to produce a 5 or 6 membered heterocyclic amine. When the heterocyclic amine is pyrrolidine and X in the aryl ring is —CH=CH—, the amide corresponds to Example 20 herein.

Thereafter, the amide of XVII is treated as the esters of formulas XIII-XXIX to produce the amides of the present invention.

The biological activity possessed by the compounds of this invention was indicated by positive results to the "LTB$_4$ Receptor Binding Assay" and the "Human Neutrophil Degranulation Assay".

Preparation of Human Neutrophils:

For use in both the "LTB$_4$ receptor Binding Assay" and the "human Neutrophil Degranulation Assay", neutrophils were purified from venous blood of normal human donors using standard techniques of dextran sedimentation, centrifugation on Histopaque$^R$ (density solution) and hypotonic lysis of erythrocytes (Boyum. A., *Isolation of Leukocytes From Human Blood: Further Observations.* Scand. J. Lab. Clin. Inves. 21 (Suppl. 97) 31, 1968). The purity of isolated neutrophils was ≥95%.

LTB$_4$ Receptor Binding Assay:

Neutrophils ($4-6\times10^6$) in 1 ml of Hanks' balanced salt solution containing 10 mM Hepes Buffer (HBSS), pH 7.4 and 30 $\mu$M nordihydroguaiaretic acid were incubated with 0.6 nM ($^3$H) LTB$_4$ in the presence or absence of test compounds. The incubation was carried out at 0° C. for 45 minutes and terminated by adding 5 ml of ice-cold HBSS followed by rapid filtration of incubation mixture under vacuum through GF/C glass fiber filters. The filters were further washed with 10 ml HBSS and their radioactivity was determined. Specific binding was defined as the difference between total binding and nonspecific binding which was not displaced by $10^{-7}$M unlabeled LTB$_4$.

The inhibition of specific binding was determined for representative compounds of this invention, and the corresponding IC$_{50}$ values calculated (Table 1). An IC$_{50}$ is the concentration of the compound of interest which will inhibit the binding of LTB$_4$ by 50% of the LTB$_4$ receptors. For example, for the compound of Example 31, the IC$_{50}$ was determined to be approximately 6.3$\mu$M.

Human Neutrophil Degranulation Assay:

LTB$_4$ induced neutrophil degranulation was determined by measuring the release of myeloperoxidase activity into the incubation medium. Neutrophils ($3\times10^6$) in 1 ml HBSS solution were preincubated with cytochalasin B(5 $\mu$g) at 37° C. for 5 minutes, followed by preincubation with test compounds for 7 minutes. Neutrophils were then incubated for 2 to 20 minutes with either LTB$_4$($5\times10^{-8}$M) or the chemotactic peptide f-met-leu-phe ($5\times10-6$M) to induce degranulation. Following incubation, samples were centrifuged and myeloperoxidase was extracted from the cell pellets by sonication in phosphate buffer containing 0.4% Triton X-100. Triton X-100 was also added to the supernatents to a concentration of 0.4%. The supernatants and the pellet extracts were then assayed spectrophotometrically for myeloperoxide activity by determining the rate of decomposition of $H_2O_2$ with o-dianisidine as hydrogen donor as described by Renlund, D. G., MacFarlane, J. L., Christensen, R. D., Lynch, R. E., and Rothstein, G., *A Quantitative And Sensitive Method For Measurement Of Myeloperoxidase*, Clinical Research 28:75A, 1980). Myeloperoxidase activity released into the supernatant was expressed as the percent of the average total activity (pellet plus supernatant).

The inhibition of LTB$_4$ induced neutrophil degranulation was determined for representative compounds of this invention and their corresponding IC$_{50}$ values were calculated (Table 1). The concentration of a compound which inhibited LTB$_4$ induced neutrophil degranulation by 50% was determined to be its IC$_{50}$ value.

By virtue of their activity as LTB$_4$ antagonists. the compounds of Formula I are useful in treating inflammatory conditions in mammals such as psoriasis, Crohn's disease, ulcerative colitis and the like. Similarly, the compounds of Formula I can be used in preventing recurring inflammatory attacks. A physician or veterinarian of ordinary skill can readily determine whether a subject exhibits the inflammatory condition. The preferred utility relates to treatment of ulcerative colitis.

The compounds of the present invention can be administered in such oral dosage forms as tablets, capsules, softgels, pills, powders, granules, elixirs, or syrups.

The compounds may also be administered intravascularly, intraperitoneally, subcutaneously, intramuscularly, or topically using forms known to the pharmaceutical art. Moreover, they may be administered rectally or vaginally, in such forms as suppositories or bougies. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, a therapeutically effective amount of one or more compounds of the present invention may be combined with any oral non-toxic pharmaceutically acceptable inert carrier such as lactose, starch, sucrose, cellulose, magnesium stearate, dicalcium phosphate, calcium sulfate mannitol, and the like, or various combinations thereof. For oral administration in liquid forms, such as in softgels, elixirs, syrups, drops and the like, a therapeutically effective amount of the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intramuscular, intraperitoneal, subcutaneous, or intramuscular administration, one or more compounds of the present invention may be combined with a suitable carrier such as water, saline, aqueous dextrose, and the like. For topical administration, such as for psoriasis, therapeutically effective amounts of one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention are ordinarily in the range of about 1.0 mg/kg up to about 21.0 mg/kg, (preferably in the range of about 2.0 to 14.0 mg/kg (orally)).

The following examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

In the following examples, and throughout this application, a wavey line ∼ defines a substituent as an asymmetric carbon having R or S stereochemistry.

CHART A

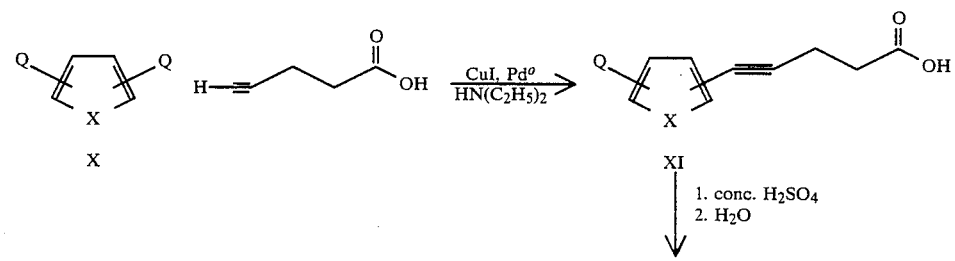

-continued
CHART A
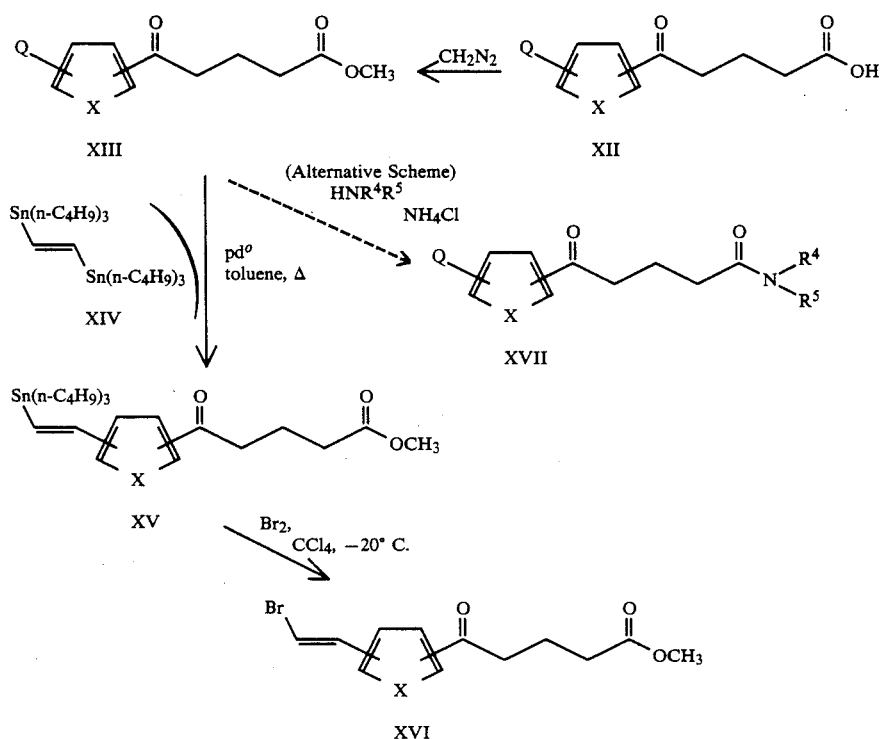
CHART B
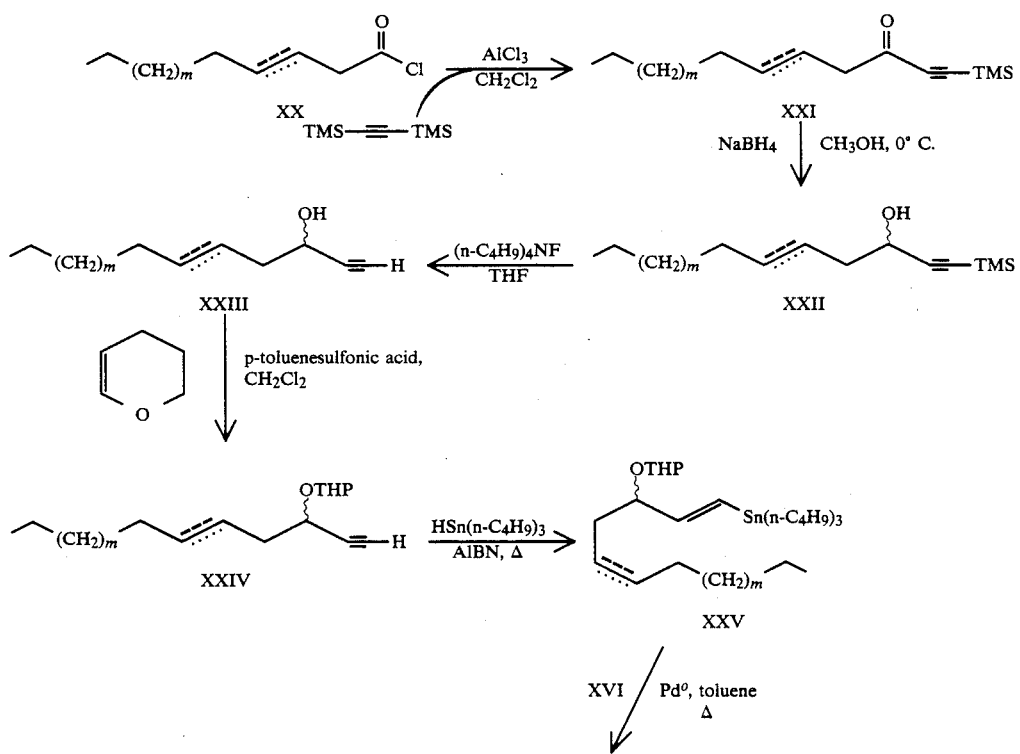

-continued
CHART B
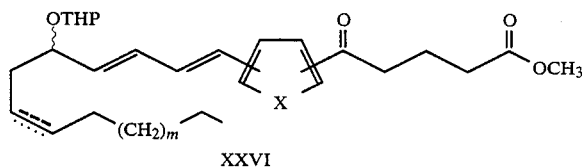
XXVI
CHART C
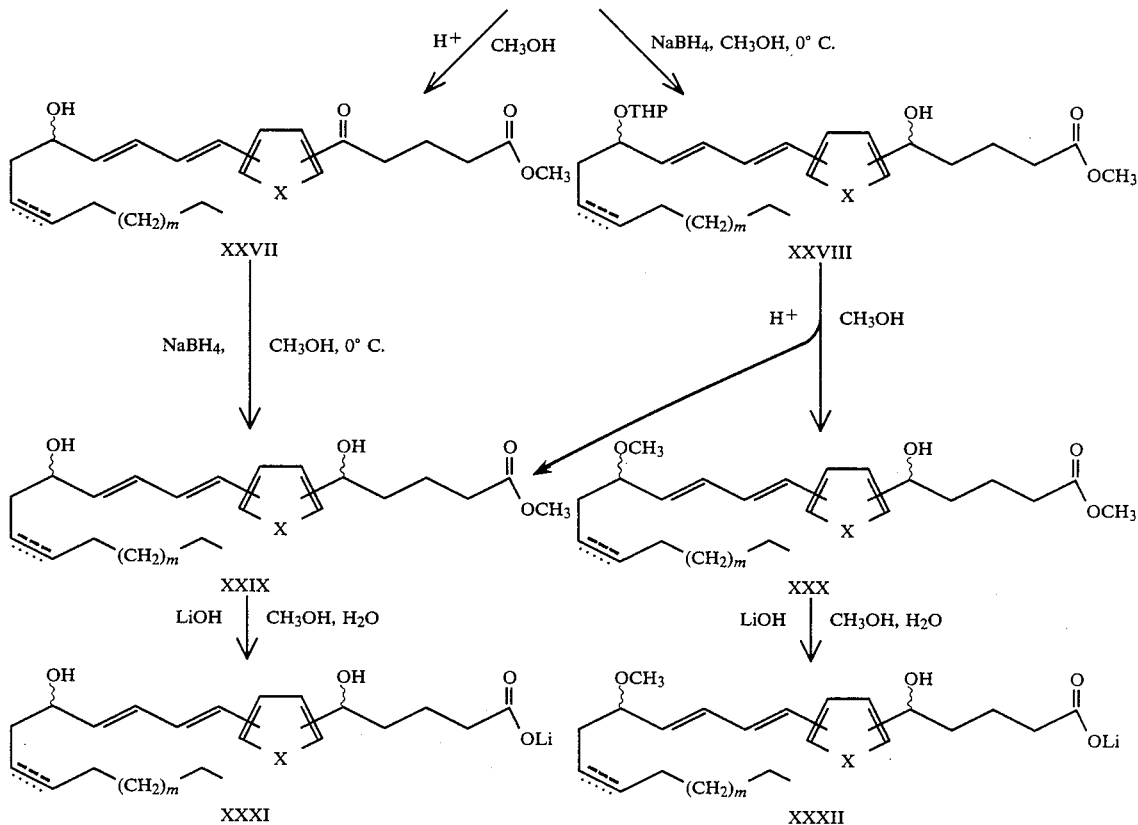
TABLE 1
Biological Activity for Representative Compounds Of The Invention
| Compound (Example No.) | Structure | Inhibition of Receptor Binding of LTB$_4$ IC$_{50}$ (uM) | Boyden Chamber Inhibition at $10^{-5}$ M (as Antagonist) | Inhibition of LTB$_4$ Induced Neutrophil Degranulation IC$_{50}$ (uM) |
|---|---|---|---|---|
| 32. | 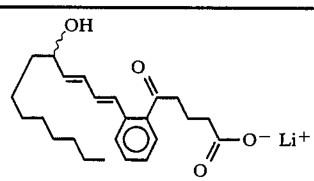 | 3.0 | 8% | 1.0 |
| 33. | 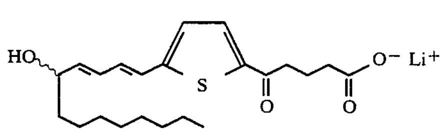 | 4.1 | 30 | 1.8 |

TABLE 1-continued

Biological Activity for Representative Compounds Of The Invention

| Compound (Example No.) | Structure | Inhibition of Receptor Binding of LTB₄ IC₅₀ (uM) | Boyden Chamber Inhibition at 10⁻⁵ M (as Antagonist) | Inhibition of LTB₄ Induced Neutrophil Degranulation IC₅₀ (uM) |
|---|---|---|---|---|
| 34. | (structure) | 6.3 | 33 | 5.2 |

DESCRIPTION OF THE PREFERRED EMBODIMENT

Example 1

5-(2-bromophenyl)-4-pentynoic acid

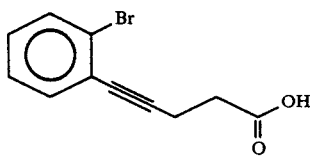

To 10 ml of diethylamine was added with stirring 0.5 g (5.1 mmol) of 4-pentynoic acid. 1.4 g (5 mmol) of 1-bromo-2-iodobenzene, and 60 mg (0.05 mmol) of tetrakis(triphenylphosphine)palladium(O). The slurry was degassed with argon and 0.19 g (1.0 mmol) of CuI was added. The reaction mixture was stirred for 2 hr. at room temperature and then poured into approximately 100 ml of a 10% HCl solution. The resulting precipitate was filtered, washed with water and dried. The solid was taken up in hot CHCl₃ and filtered to remove insoluble salts. After evaporation of the solvent, the resulting orange solid was recrystallized from a chloroform-hexane mixture to produce a tan solid, m.p. 87–91° C.

Acetone-d₆
¹H NMR δ (300 MHZ)
TMS
7.62(dd, 1H); 7.48(dd, 1H); 7.35(dt, 1H); 7.25(dt, 1H); 2.75(m, 2H); 2.65(m, 2H).

Example 2

2-bromo-δ-oxobenzenepentanoic acid

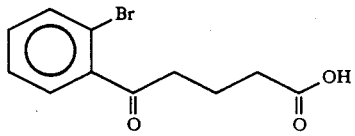

Into 20 cc of concentrated H₂SO₄ was dissolved 0.1 g (0.4 mmol) of the product of Example 1 to give a brown solution. The solution was allowed to stand at room temperature for 10 minutes. Thereafter, the solution was cooled to 0° C. in an ice bath and ice was then added to it. The solution was then diluted with water and extracted twice with ethyl acetate. The combined extracts were sequentially washed once each with water and brine and then dried (MgSO₄). Removal of the solvent under reduced pressure produced a yellow oil which was used without further purification.

CDCl₃
¹H NMR δ (300 MHZ):
TMS 7.60(d, 1H); 7.4–7.2(m, 3H); 3.0(t, 2H); 2.5(t, 2H); 2.05(p 2H).

Example 3 methyl 2-bromo-δ-oxobenzenepentanoate

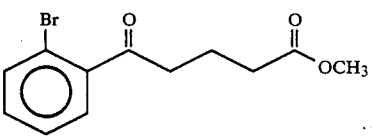

To 0.54 g (2.0 mmol) of the product of Example 2 dissolved in ether was added an ethereal solution of excess diazomethane at 0° C. to produce a 97% yield of the ester as a yellow oil. The ester was used without further purification.

CDCl₃
¹H NMR δ (300 MHZ):
TMS
7.60(d, 1H); 7.40–7.25(m, 3H); 3.68(s, 3H); 2.99(t, 2H);
2.45(t, 2H); 2.06(p, 2H).

Example 4 methyl 2-(2-bromo-E-ethenyl)-δ-oxobenzenepentanoate

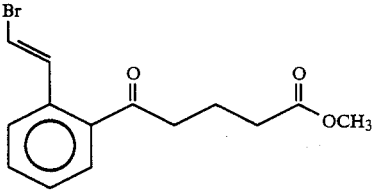

To 10 ml of toluene was added 6.0 g (9.9 mmol) of trans-1,2-bis(tri-n-butylstannyl)ethylene, which was prepared according to the procedure of Corey, et al., J. Org. Chem. 40, 3788 (1975), and 0.5g (1.8 mmol) of the product of Example 3. To the solution was then added 0.040 g (0.035 mmol) of 2 mole% tetrakis(triphenylphosphine)palladium(O) and the solution was degassed with argon. The reaction mixture was heated under argon for 1 hour at 120° C. (oil bath). Thereafter, the reaction mixture was cooled to −20° C. To the reaction mixture was added dropwise with stirring, a solution of 1.5 ml (29.1 mmol) of Br₂ in 30 ml of CCl₄ until thin layer chromatography of the reaction mixture indicated that all of the product of Example 3 was consumed. The volatile components were removed in vacuo. The residue was flash chromatographed on a silica gel column. Sequential elution with hexane, 5% diethyl ether in hexane, and 10% diethyl ether in hexane produced 0.48 g of the titled product. The product was triturated with cold hexane to give a white solid, m.p. 52-55° C.

Analysis for $C_{14}H_{15}O_3Br$ (MW=310.9):
Calcd.: C, 54.04; H, 4.89; Br, 25.68.
Found: C, 53.59; H, 4.86; Br, 25.25.

Example 5

1-(trimethylsilyl)-1-undecyn-3-one

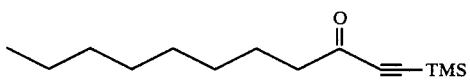

To 500 ml of $CH_2Cl_2$ was added 53 ml (294 mmol) of nonanoyl chloride and 50 g (293.4 mmol) of bis(trimethylsilyl)acetylene. The reaction mixture was cooled in an ice bath and 40 g (300 mmol) of $AlCl_3$ was added portionwise with stirring over ½ hour. After stirring for an additional hour, the reaction mixture was quenched with ice. Water was added to the reaction mixture and it was extracted 3× with 200 ml aliquots of diethyl ether. The combined extracts were washed 2× with 50 ml aliquots of saturated $NaHCO_3$, 1× with brine, and then dried ($MgSO_4$). The solvent was removed in vacuo to give a brown oil which was used without further purification.

$CDCl_3$
$^1H$ NMR $\delta$ (300 MHZ)
TMS
2.45(t, 2H); 1.55(m, 2H); 1.20(br s, 10H); 0.80(t, 3H); 0.15(s, 9H).

Example 6

1-(trimethylsilyl)-1-undecyn-3-ol

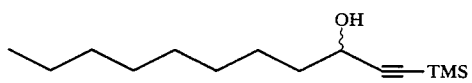

To 200 ml of methanol was added 10 g (41.93 mmol) of the product of Example 5. The reaction mixture was cooled to 0° C. and 0.53 g (14 mmol) of $NaBH_4$ was added portionwise over 5 minutes. After an additional 15 minutes, the reaction was quenched with acetone and the solvent removed under reduced pressure. The residue was partitioned between water and diethyl ether. The aqueous layer was extracted one additional time with diethyl ether and the combined organic extracts were washed 1× with brine and then dried ($MgSO_4$). Thin layer chromatography indicated the crude product to contain both the titled product and its unsilylated analogue. This was used in the next step without further purification.

Mixture:

$CDCl_3$
$^1H$ NMR $\delta$ (300 MHZ):
TMS
4.38(m, 1H); 2.48(d, 1H); 2.03(br.d, 1H); 1.95(br.d, 1H);
1.72 (m, 2H); 1.45(m, 2H); 1.28(m. 10H); 0.87(t, 3H); 0.19(s, 9H).

Example 7

1-undecyn-3-ol

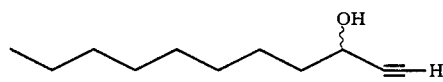

To 8.65 g of the crude product from Example 6 was added 40 ml of 1M $(n-C_4H_9)_4NF$ in tetrahydrofuran (THF). The reaction mixture became warm and stirring was continued at room temperature for ½ hour. Thereafter, the reaction mixture was poured into brine and extracted 2× with diethyl ether. The combined ether extracts were washed 2× with brine and then dried ($MgSO_4$). Removal of the solvent produced a brown oil. The oil was flash chromatographed on a silica gel column. Gradient elution from 10% diethyl ether in petroleum ether to 20% diethyl ether in petroleum ether produced 6.81 g of the titled product as a yellow oil.

Analysis for $C_{11}H_{20}O$ (MW=168.0):
Calcd.: C, 78.51; H, 11.78.
Found: C, 78.02; H, 12.43.
$CDCl_3$
$^1H$ NMR $\delta$ (300 MHZ):
TMS
4.38(dt, 1H); 2.45(dd, 1H); 2.04(br d, 1H); 1.7(m, 2H); 1.45(m, 2H); 1.3(br. s, 10H); 0.88(t, 3H).

Example 8

2-[(1-ethynylnonyl)oxy]tetrahydro-2H-pyran

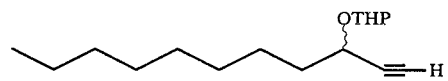

THP = tetrahydropyranyl

To 100 ml of $CH_2Cl_2$ was added 6.81 g (40.5 mmol) of the product of Example 8, 11 ml (120 mmol) of dihydropyran, and 100 mg of p-toluenesulfonic acid. After 6 hours at room temperature, the reaction mixture still contained primarily starting material. The reaction mixture was stripped of all volatile materials and recharged with 10 ml of dihydropyran. After stirring overnight, the reaction mixture was heated for 6 hr. at 80° C. Although thin layer chromatography indicated that some starting material was still present, the reaction mixture was cooled and diluted with diethyl ether. The diluted reaction mixture was washed 1× with saturated $NaHCO_3$ and then dried ($K_2CO_3$). The solvent was stripped in vacuo and the residue chromatographed on a silica gel column. Elution of the column with 10% diethyl ether in petroleum ether yielded 3.12 g of the titled product.

$CDCl_3$
$^1H$ NMR $\delta$ (300 MHZ):
TMS
4.98, 4.75(t, 1H); 4.4, 4.28(dt, 1H); 4.02. 3.80(m, 1H); 3.54(m, 1H);
2.44, 2.38(d, 1H); 2.0,-1.4(m, 8H); 1.3(br. s, 12H); 0.89(t, 3H).

Example 9 tetrahydro-2-[[1-[2-(tributylstannyl)-E-ethenyl]nonyl]oxy]-2H-pyran

-continued

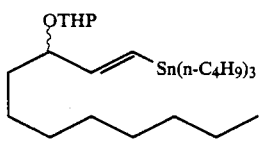

THP = tetrahydropyranyl

To 0.05 g (0.19 mmol) of the titled product of Example 8 is added 0.6 ml (0.22 mmol) of tri-n-butyltin hydride, and 20 mg of azoisobutyronitrile (AIBN). The reaction mixture was heated at 110° C. for 3 hours, whereupon thin layer chromatography indicated that the reaction was complete, producing the titled product. The product was used without further purification.

Example 10 methyl δ-oxo-2-[5-[(tetrahydro-2H-pyran-2-yl)oxy]-1E, 3E-tridecadienyl]benzenepentanoate

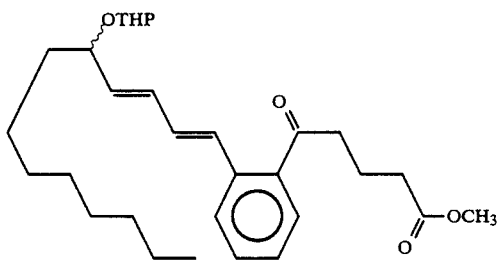

THP = tetrahydropyranyl

To 1 ml of toluene was added 0.1 g (0.35 mmol) of the product of Example 4, 0.11 g (0.38 mmol) of the product of Example 9, and 5.0 mg of tetrakis(triphenylphosphine)palladium(O). The solution was degassed with argon and then heated at reflux under argon for approximately 5 hours. The reaction mixture was then cooled to room temperature and flash chromatographed. Gradient elution with hexane, 1% diethyl ether in hexane, 5% diethyl ether in hexane, and 10% diethyl ether in hexane produced 0.90 mg (0.19 mmol) of the titled product.

CDCl$_3$
$^1$H NMR (300 MHZ):
TMS 7.58(m, 2H); 7.43(m, 1H); 7.30(m, 1H); 6.98(dd, 1H); 6.68(m, 1H);

6.35(m, 1H); 5.86(dd)+5.63(dd)(1H); 4.71(t)+4.66(t)(1H);

4.15(m, 1H); 3.90(m, 1H); 3.66(s, 3H); 3.49(m, 1H); 2.95(dt, 2H);

2.42(t, 2H); 2.05(m, 2H); 1.9–1.2(complex m, 20H); 0.85(t, 3H).

Example 11 methyl 2-(5-hydroxy-1E,3E,-tridecandienyl)-δ-oxobenzenpentanoate

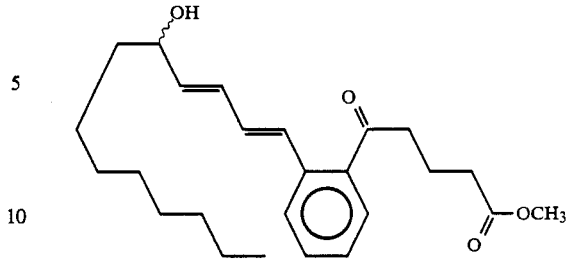

To 1 ml of a 3:1:1 solution of acetic acid, water, and tetrahydrofuran (THF) was added 20 mg (0.041 mmol) of the titled product of Example 10 and the reaction mixture was allowed to stir 16 hr. After this time, some insoluble oil was still present and approximately 50 μl of THF was added to the reaction mixture and it was stirred for an additional 2 hours. The volatile components were removed in vacuo and the residue was flash chromatographed. Elution with 1:1 diethylether-hexane produced 10 mg of the desired product.

CDCl$_3$
$^1$H NMR δ (300 MHZ):
TMS 7.58(m, 2H); 7.43(t, 1H); 7.3(m, 1H); 6.99(d, 1H); 6.65(dd, 1H);

6.42(dd, 1H); 5.85(dd, 1H); 4.20(m, 1H); 3.68(s, 3H); 2.95(t, 2H).

2.42(t, 2H); 2.05(p, 2H); 1.55(m, 2H); 1.25(br. s, 12H); 0.88(t, 3H).

Example 12 methyl δ-hydroxy-2-[5-[(tetrahydro-2H-pyran-2-yl)oxy]-1E,3E-tridecadienyl]benzenepentanoate

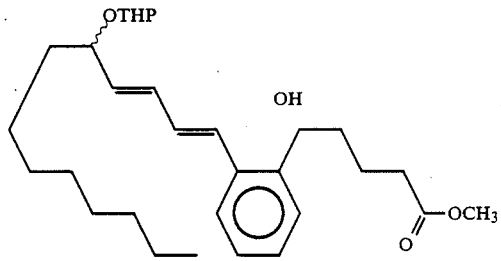

THP = tetrahydropyranyl

To 3 ml of methanol was added 0.1 g (0.21 mmol) of the titled product of Example 10. The reaction mixture was cooled to 0° C. and 3mg of NaBH$_4$ was added. After 30 minutes, the reaction was complete. The reaction mixture was quenched with acetone and the volatile components were removed in vacuo. The residue was partitioned between diethyl ether (ether) and water. The organic layer was separated and the aqueous layer was extracted once more with ether and the combined extracts were washed with brine and dried (K$_2$CO$_3$). Removal of the solvent produced 0.11 g of a pale yellow oil. The product of this reaction was used without further purification.

CDCl$_3$ $^1$H NMR (300 MHZ):
TMS 7.48(m, 2H); 7.23(m, 2H); 6.83(dd, 1H); 6.65(m, 1H); 6.39(m, 1H);

5.86(dd) +5.62(dd)(1H); 5.02(br.s., 1H); 4.70(m, 1H); 4.15(m, 1H)., 3.89(m, 1H); 3.64(s 3H); 3.49(m, 1H); 2.33(t, 2H); 2.10(m, 1H);

1.90–1.15(complex m, 24H); 0.85(t, 3H).

Example 13 methyl δ-hydroxy-2-(5-hydroxy-1E,3E-tridecadienyl)benzenepentanoate

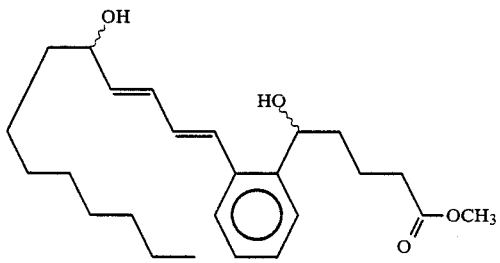

To 3 ml of methanol is added 0.1 g (0.21 mmol) of the titled product of Example 12 and 10 mg of p-toluenesulfonic acid. The reaction mixture is heated to 55° C. for 3 hours. The solvent was removed under reduced pressure and the residue was flash chromatographed on silica gel column. Elution with 2:1 diethyl ether hexane produced 3 bands. The third band contained 0.030 g of the titled products which was collected as fractions 8-18.

CDCl$_3$
$^1$H NMR δ (300 MHZ)
TMS 7.48(m, 2H); 7.25(m, 2H); 6.86(d, 1H); 6.65(dd, 1H); 6.43(dd, 1H);

5.84(dd, 1H); 5.02(t, 1H); 3.65(s, 3H); 3.63(m, 1H); 2.35(t, 2H);

2.0–1.2(complex, 20H); 0.88(t, 3H).

Example 14 methyl 3-(1E,3E-dodecadienyl)-1,3-dihydro-1-isobenzofuranbutanoate

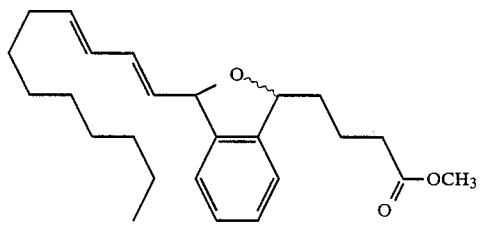

Isomer A & B

The first band which was eluted from the column in Example 13 was further purified on high pressure liquid chromatography (HPLC). Fractions 20–23 from the HPLC produced 0.010 g of a 5:1 mixture of isomers A and B. Fractions 24–29 from the HPLC produced 0.0044 g of pure isomer B.

Isomer A

CDCl$_3$
$^1$H NMR δ (300 MHZ):
TMS 7.26(m, 2H); 7.13(m, 2H); 6.33(dd, 1H); 6.03(dd, 1H); 5.78(m, 1H);

5.60(m, 2H); 5.33(m, 1H); 3.66(s, 3H); 2.38(t, 2H); 2.07(m, 2H);

1.78(m, 4H); 1.38(m, 2H); 1.28(br. s, 10H); 0.89(t, 3H).

Isomer B

CDCl$_3$
$^1$H NMR δ (300 MHZ):
TMS 7.27(m, 2H); 7.14(m, 2H); 6.36(dd, 1H); 6.06(dd, 1H); 5.78(m, 1H);

5.55(m, 2H); 5.20(m, 1H); 3.66(s, 3H); 2.39(t, 2H); 2.09(q, 2H);

1.85(m, 4H); 1.39(m, 2H); 1.28(br. s, 10H); 0.89(t, 3H).

Example 15 methyl δ-hydroxy-2-(5-methoxy-1E,3E-tridecadienyl)benzenepentanoate

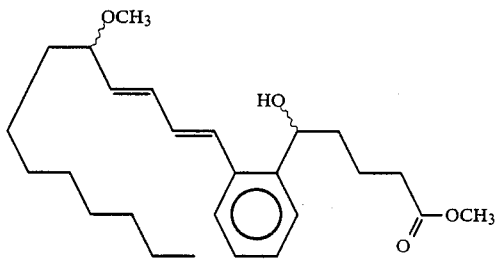

The titled compound was prepared and worked up according to the procedure of Example 13. Flash chromatography of the reaction mixture produced 3 bands when the column was eluted with 2:1 diethyl ether-hexane. The second band, which was eluted as fractions 4-6, produced 0.030 g of the titled product upon evaporation of the solvent.

CDCl$_3$
$^1$H NMR δ (300 MHZ):
TMS 7.49(m, 2H); 7.25(m, 2H); 6.87(d, 1H); 6.65(dd, 1H); 6.38(dd, 1H);

5.65(dd, 1H); 5.03(m, 1H); 3.66(s, 3H); 3.40(m, 1H); 3.30(s, 3H);

2.36(t, 2H); 2.03(d, 1H); 1.9–1.4(complex, 6H); 1.28(br. s., 12H);

0.88(t, 3H).

Example 16

δ-hydroxy-2-(5-hydroxy-1E,3E-tridecadienyl) benzenepentanoic acid, lithium salt

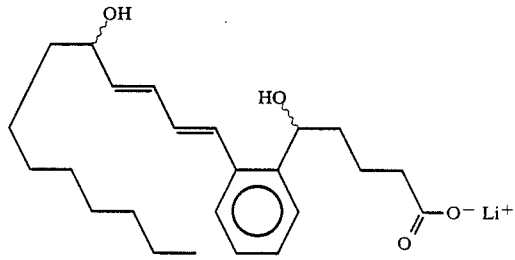

To 0.3 ml of methanol was added 0.0065 g (0.0162 mmol) of the titled compound from Example 13. The solution was cooled to 0° C. (ice bath) and 0.1 ml of H₂O was added followed by 20 μl of 1M LiOH (0.02 mmol). The mixture was stirred as a slurry for 5 minutes and the ice bath was removed. Stirring was continued overnight. The reaction mixture was then concentrated with a stream of N₂ plus the last traces of solvent were removed at high vacuum to afford the title compound.

Example 17

3-(1E,3E-dodecadienyl)-1,3-dihydro-1-isobenzofuranbutanoic acid, lithium salt, isomer A

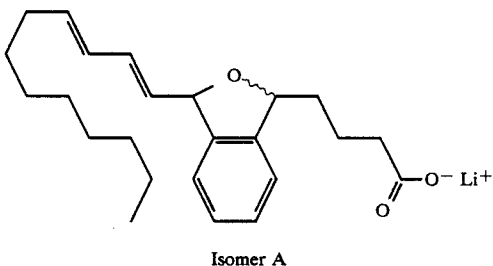

Isomer A

The titled compound was prepared by reacting 0.0047 g of isomer (A) containing approximately 16% of Isomer B, the upper fraction of Example 14, according to the procedure of Example 16, using 15 μl of 1M LiOH instead of 20 μl of 1M LiOH.

This produced the lithium salt as a 5:1 mixture of Isomers A and B.

Example 18

3-(1E,3E-dodecadienyl)-1,3-dihydro-1-isobenzofuranbutanoic acid, lithium salt, isomer B

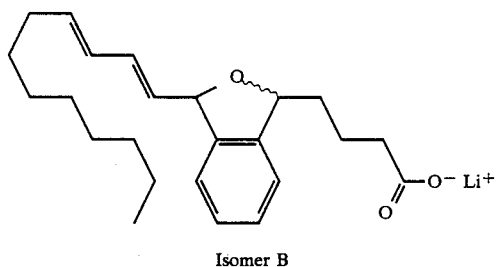

Isomer B

The titled compound was prepared by reacting 0.0016 g of isomer B, the lower fraction of Example 14, according to the procedure of Example 16, using 6 μl of 1M LiOH instead of 20 μl of 1M LiOH.

Example 19

δ-hydroxy-2-(5-methoxy-1E,3E-tridecadienyl)benzenepentanoic acid, lithium salt

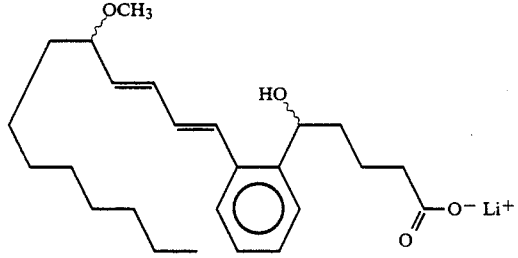

The titled compound was prepared by reacting 0.0041 g of the product of Example 15 according to the procedure of Example 16, using 11 μl of 1M LiOH instead of 20 μl of 1M LiOH.

Example 20

1-[5-(2-bromophenyl)-1,5-dioxopentyl]pyrrolidine

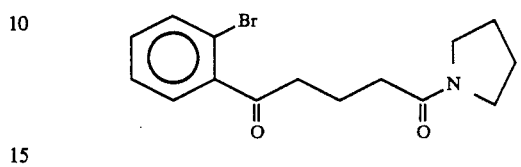

To 1 ml of pyrrolidine is added with stirring .100 g (0.35 mmol) of the product of Example 3 and 5mg of NH₄Cl. The combined reagents were stirred in a sealed tube for 16 hours at room temperature. After this time, an additional 1 ml of pyrrolidine and 5 mg of NH₄Cl was added and the reaction mixture was stirred an additional 16 hours. The solvent was removed under reduced pressure and the residue was flash chromatographed. Elution with diethyl ether produced 0.13 g of the titled product, which was used without further purification.

CDCl₃
¹H NMR δ (300 MHZ):
TMS
7.59(dd, 1H); 7.45-7.25(m, 3H); 3.44(m, 4H); 3.04(t, 2H);
2.49(t, 2H); 2.06(p, 2H); 1.89(m, 4H).

Example 21

1-[5-[2-(2-bromo-E-ethenyl)phenyl]-1,5-dioxopentyl]pyrrolidine

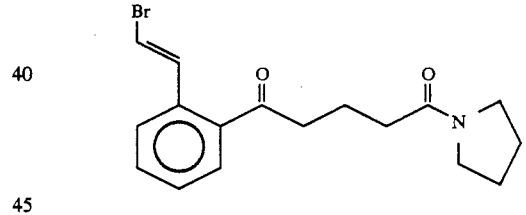

To 1 ml of toluene was added 0.13 g (0.40 mmol) of the titled product from Example 20, 0.36 g (0.60 mmol) of trans-1,2-bis-(tri-n-butylstannyl)ethylene, and 9 mg (0.008 mmol) of tetrakis(triphenylphosphine)palladium(0). The solution was degassed with argon and heated at 120° C. for 1 hour. The reaction was cooled to −20° C. and treated with Br₂ in CCl₄ according to the procedure of Example 4. Upon evaporation of the volatile components in vacuo the reaction mixture produced a gummy yellow solid. The gummy solid was triturated with ether to produce 0.11 g of a yellow solid, which was used without further purification.

CDCl₃
¹H NMR δ (300 MHZ):
TMS
7.75-7.30(m, 5H); 6.63(d, 1H); 3.45(p, 4H); 3.03(t, 2H);
2.35(t, 2H); 2.05(p, 2H); 1.90(m, 4H).

Example 22

1-(tributylstannyl)-1E-undecen-3-ol

-continued

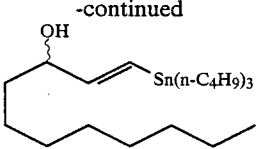

To 0.07 g (0.42 mmol) of the titled product of Example 7 is added 0.15 g (0.5 mmol) of tri-n-butyltin hydride and 20 mg of azoisobutyronitrile (AIBN). The reaction mixture was heated to 120° C. for 2 hours. Afterwards, it was cooled to room temperature and pumped at high vacuum overnight. The crude reaction mixture was then heated to 90° C. and maintained at high vacuum for 2 additional hours. Upon cooling to room temperature, the crude product was used as is.

Example 23

1-[5-[2-(5-hydroxy-1E,3E-trideccadienyl)-phenyl]-1,5-dioxopentyl]pyrrolidine

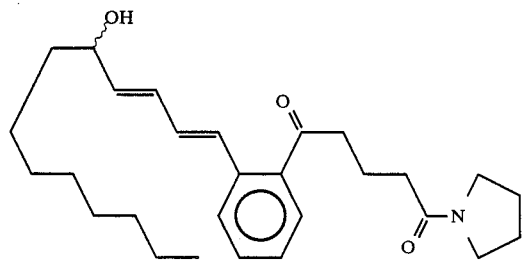

To 2 ml of toluene is added all of the crude residue from Example 22, 0.11 g (0.31 mmol) of the product from Example 21, and 10 mg of tetrakis(triphenylphosphine)palladium(O). The solution was degassed with argon, and then heated to reflux under argon for approximately 5 hours. Afterwards, the reaction mixture was cooled to room temperature and flash chromatographed. Gradient elution beginning with diethyl ether (ether) and going to 1:1 ether-ethyl acetate, produced the titled product. The product was used without purification.

CDCl$_3$
$^1$H NMR δ (300 MHZ)
TMS 7.75-7.25(m, 4H); 7.0(d,1H); 6.65(dd, 1H); 6.40(dd, 1H); 5.85(dd, 1H);

4.19(m, 1H); 3.41(m, 4H); 3.01(m, 2H); 2.38(t, 2H); 2.05(p, 2H);

1.90(m, 4H); 1.6(m, 2H); 1.30(br. m, 12H); 0.89(t, 3H).

Example 24

1-[5-hydroxy-5-[2-(5-hydroxy-1E,3E-tridecadienyl)phenyl]-1-oxopentyl]pyrrolidine

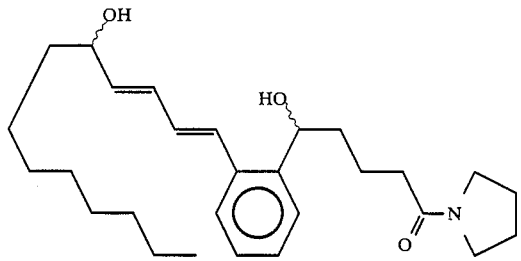

The crude residue from Example 23 was taken up in 2 ml of methanol and cooled to 0° C. 11 mg (0.3 mmol) of NaBH$_4$ was added portionwise until thin layer chromatography (TLC) of the reaction mixture showed no starting material remaining. The solvent was removed under reduced pressure and the residue was flash chromatographed using 1:1 diethyl ether/ethyl acetate as the eluent. The later eluting fractions were collected, combined, and the solvent removed under reduced pressure. The residue was again flash chromatographed. Elution with diethyl ether followed by tetrahydrofuran produced 0.01295 g of the titled product.

CDCl$_3$
$^1$H NMR δ (300 MHZ):
TMS 7.49(m, 2H); 7.24(m, 2H); 6.85(dd, 1H); 6.65(dd, 1H); 6.41(dd, 1H);

5.83(dq, 1H); 5.0(t, 1H); 4.19(q, 1H); 3.44(t, 2H); 3.38(t, 2H);

2.30(t, 2H); 2.0-1.6(m, 10H), 1.55(m, 2H); 1.30(br. s, 10H); 0.88(t, 3H).

Example 25

5-(5-iodo-2-thienyl]-4-pentynoic acid

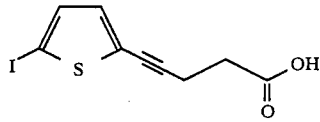

To 75 ml of diethylamine was added with stirring 3.76 g of 4-pentynoic acid, 22 g of 2,4-diiodothiophene, and 300 mg of tetrakis-(triphenylphosphine)palladium(o). The slurry was degassed with argon and 960 mg of CuI was added. The slurry was maintained under argon and allowed to stir overnight, producing a dark brown solution. Thereafter, the solvent was removed under reduced pressure and 100 ml of 10% HCl was added to the residue. The residue was filtered and then extracted 3× with ethyl acetate. The combined extracts were washed 1× with water, dried over anhydrous MgSO$_4$, filtered, and stripped. The resulting residue was flash chromatographed on a column of silica gel. Elution with a mixture of 30/70/2 parts ethyl acetate/hexane/acetic acid produced 3.5 g of the titled product as a yellow solid.

Analysis for C$_9$H$_7$IO$_2$S (MW=306.12):
Calcd: C, 35.31; H, 2.31; I, 41.46.
Found: C, 35.44; H, 2.30; I, 41.37.

Example 26

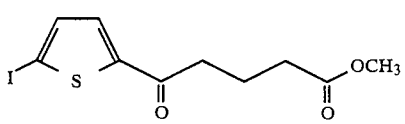

To 2.0 g of the product from Example 25 was added 150 ml of cooled (ice bath) concentrated H$_2$SO$_4$. The reaction mixture was stirred and shaken for 10 minutes. Thereafter the reaction mixture was poured onto 800 g of crushed ice. The resulting solid was filtered and washed 3× with H$_2$O. The solid was dissolved in ethyl acetate, dried over anhydrous MgSO$_4$, filtered, and the solvent removed under reduced pressure. To the resulting green solid (ketoacid) was added a solution of ethereal diazomethane. The mixture was swirled until all the solid was dissolved and the solution was allowed to stand overnight at room temperature. The solvent was then removed under reduced pressure and the residue flash chromatographed. Elution with 20/80 ethyl acetate/hexane produced 1.2 g of the titled product as a white solid.

CDCl$_3$
$^1$H NMR δ (300 MHZ):
TMS
7.34(d, 1H); 7.30(d, 1H); 3.69(s, 3H); 2.93(t, 2H); 2.44(t, 2H); 2.05(m, 2H).

Example 27

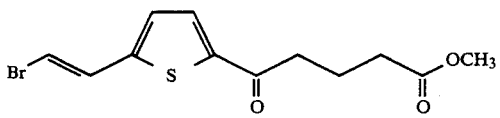

To 20 ml of toluene was added 950 mg of the titled product from Example 26, and 3.4 g of trans-1,2-bis-(tri-n-butylstannyl)ethylene. The flask was degassed with argon and 69 mg of tetrakis-(triphenylphosphine)Pd(O) was added. The flask was sealed, heated to 120° C. (oil bath) for 20 minutes, producing a dark brown solution containing the trans-stannylvinylthiophene substitution product. The flask was then cooled to −25° C. (dry ice/isopropyl alcohol) and approximately 3 ml of a solution containing 1.5 ml Br$_2$ in 30 ml CCl$_4$ was added dropwise with stirring until all the trans-vinylstannyl-thiophene was consumed. The reaction mixture was worked up and chromatographed as in Example 4 to produce 250 mg of a pale yellow solid, which was a mixture of the titled product and the trans-iodovinylthiophene analogue.

CDCl$_3$
$^1$NMR δ (300 MHZ):
TMS
7.59(d, 1H); 7.18(d, 1H); 6.97(d, 1H); 6.86(d, 1H); 3.69(s, 3H); 2.97(t, 2H); 2.45(t, 2H); 2.06(m, 2H).

Example 28

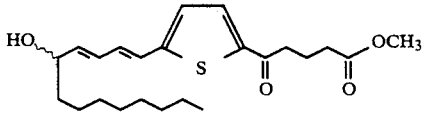

The oil from Example 22 was taken up in 10 ml of toluene. To this solution was then added 200 mg of the product mixture from Example 27 and 15 mg of tetrakis-(triphenylphosphine)palladium(O). The reaction mixture was heated with stirring to 120° C. (oil bath) for 2 hours. Thereafter, the solvent was removed under reduced pressure and the residue was flash chromatographed on a silica gel column. Elution with 1:9 ethyl acetate/hexane produced 65 mg of the titled product as a liquid.

CDCl$_3$
$^1$H NMR δ (300 MHZ):
TMS
7.58(d, 1H); 6.95(d, 1H); 6.79–6.57(m, 2H); 6.35(dd, 1H); 5.93(dd, 1H);
4.21(m, 1H); 3.69(s, 3H); 2.94(t, 2H); 2.43(t, 2H); (2.05(m, 2H);
1.58(m, 2H); 1.29(m, 2H); 0.93(t, 3H).

Example 29

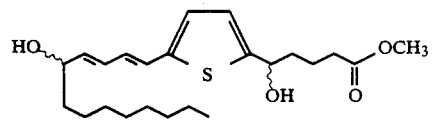

Into 3 ml of methanol was dissolved 50 mg of the titled product of Example 28 . The methanol solution was cooled to 0° C. (ice bath) and 5 mg of NaBH$_4$ was added. The reaction mixture was stirred for 1 hour at 0° C. and then quenched with acetone. The solvent was removed from the quenched reaction mixture under reduced pressure. Water was added to the residue and it was extracted 3× with ethyl acetate. The combined extracts were dried MgSO$_4$, filtered, and the solvent removed under reduced pressure. The oily residue was chromatographed on a silica gel column. Elution with 3:7 ethyl acetate:hexane produced 35 mg of the titled product as a light yellow oil.

Analysis for $C_{23}H_{36}O_4S$ (MW=408.65).
Calcd.: C, 67.60; H, 8.88.
Found: C, 67.24; H. 9.02.
CDCl$_3$
$^1$H NMR δ (300 MHZ)
TMS
6.80(dd, 2H); 6.65–6.45(m, 2H); 6.28(dd, 1H); 5.76(dd, 1H); 4.85(m, 1H);
4.17(m, 1H); 3.67(s, 3H); 2.37(t, 2H); 1.94–1.62(m, 4H); 1.56(m, 2H);
1.42–1.1(m, 12H); 0.88(t, 3H).

Example 30

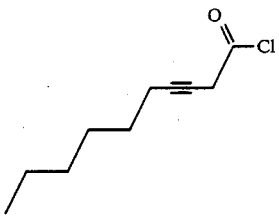

To 6.8 g (70 mmol) of 3-butynoic acid dissolved in 150 ml of 1:1 tetrahydrofuran (THF):hexamethyl phosphoric triamide (HMPA) and cooled to −20° C. is added via syringe a solution of n-butyl lithium in hexane (1.6N, 2 equiv). The mixture was allowed to warm to 0° C. The mixture is stirred for 30 minutes at this temperature and then 150g (1.1 equiv) of 1-iodohexane is added dropwise as a solution in 20 ml of THF. The mixture is allowed to warm to room temperature and then is partitioned between ether and water. The aqueous layer is acidified with 3N H$_2$SO$_4$ and extracted with ether. The combined organic extracts are washed with brine and dried (Na$_2$SO$_4$). Evaporation of the volatiles in vacuo and chromatography of the crude on silica gel (ethyl acetate/hexane/acetic acid; 10:90:0.1) affords 4.5 g of pure 3-decynoic acid.

The 3-decynoic acid is converted to its corresponding acyl chloride by reaction with thionyl chloride.

Example 31

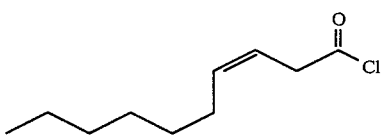

To 4.5 g (27 mmol) of 3-decynoic acid from Example 30 dissolved in methanol in a Paar bottle is added 2 mg of nickel boride as catalyst. The bottle is flushed with hydrogen, sealed and pressurized with $H_2$ at 2 pounds per square inch. The hydrogenation is allowed to proceed at room temperature for 2 hours. The methanol is stripped in vacuo and the residue is partitioned between ethyl acetate and in HCl. The ethyl acetate layer is separated, dried, ($Na_2SO_4$) and is stripped to afford an almost quantitative yield of 3-decenoic acid.

The 3-decenoic acid was converted to its corresponding acyl chloride (3-decenoyl chloride) by reaction with thionyl chloride.

Example 32

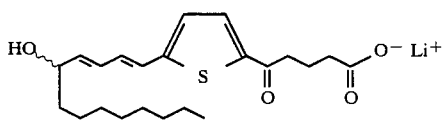

To 0.3 ml of methanol was added 3.2 mg (0.0078 mmol) of the title compound from Example 28. To this solution was added 0.1 cc of water followed by 7.8 μl of 1M LiOH and the mixture was stirred at R. T. overnight. Thereafter, the reaction mixture was concentrated with a stream of $N_2$ and the last trace of solvent was removed at high vacuum to afford the title compound.

Example 33

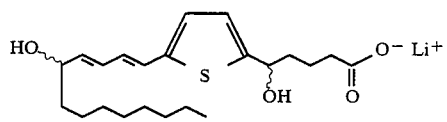

The title compound was prepared by reacting 4.0 mg of the product of Example 29 according to the procedure of Example 32 using 12 μl of 1M LiOH instead of 7.8 μl of 1M LiOH.

Example 34

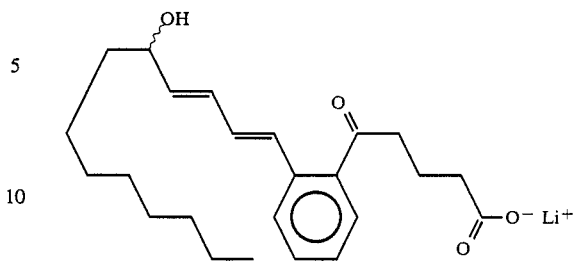

To 0.3 ml of methanol was added 2.36 mg (0.0059 mmol) of the title compound from Example 11. To this solution was added 0.2 ml of water followed by 7.8 μl of 1M LiOH and the mixture was stirred at room temperature (R. T.) overnight. Thereafter, the reaction was worked up as in Example 32 to produce the title product.

What is claimed is:

1. A compound of the formula:

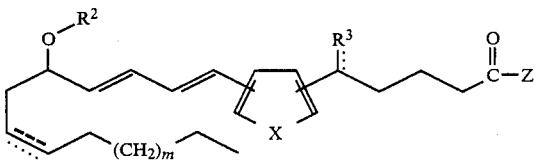

or a pharmaceutically acceptable salt thereof
wherein X is —CH=CH—;
wherein Z is —NR$^4$R$^5$;
wherein R$^2$ is H, —CH$_3$ or —C$_2$H$_5$;
wherein R$^3$ is OH, H or =O; and
wherein R$^4$ and R$^5$ may independently be hydrogen, or lower alkyl having 1-6 carbon atoms.

2. A compound according to claim 1 of the formula

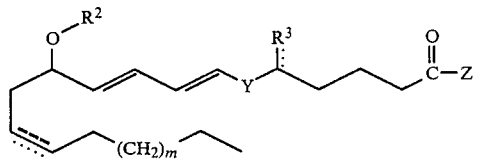

or a pharmaceutically acceptable salt thereof, wherein Y is

wherein Z is —NR$^4$R$^5$;
wherein R$^2$ is —CH$_3$ or —C$_2$H$_5$;
wherein R$^3$ is OH, H or =O; and
wherein R$^4$ and R$^5$ may independently be hydrogen, or lower alkyl having 1-6 carbon atoms.

3. A pharmaceutical composition comprising a therapeutically or prophylactically effective amount of a compound according to claim 1 in a pharmaceutically acceptable carrier.

4. A pharmaceutical composition according to claim 3 wherein said composition is in oral dosage form.

5. A method of treating inflammatory conditions in mammals comprising administering to a patient in need of such treatment, a therapeutically effective amount of pharmaceutical composition according to claim 3.

6. A method of preventing an inflammatory attack in mammals comprising administering to a patient susceptible to such attack a prophylactically effective amount of a compound according to claim 1 in a pharmaceutically acceptable carrier.

* * * * *

UNITED STATES PATENT AND TRADEMARK OFFICE
CERTIFICATE OF CORRECTION

PATENT NO. : 4,971,997
DATED : Nov. 20, 1990
INVENTOR(S) : Djuric, et. al.

It is certified that error appears in the above-identified patent and that said Letters Patent is hereby corrected as shown below:

Page 1, ABSTRACT, the structure reading

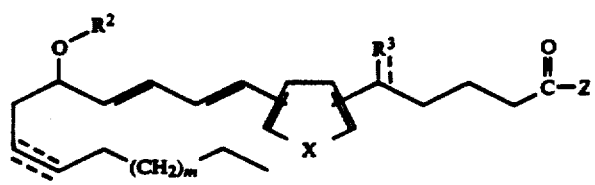

should read

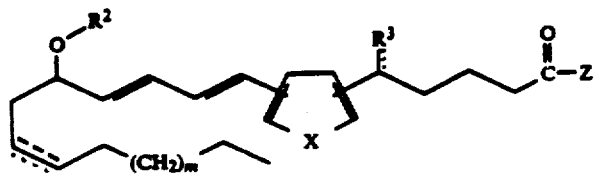

Column 3, line 18, reading ":" should be deleted.

Column 3, line 20, reading "wherein $R^3$, $R^4$, $R^5$," should read -- $R^1$, $R^2$, $R^3$, $R^4$, $R^5$, --.

Column 4, line 15, reading "long,. i.e." should read -- long, i.e. --.

Column 5, line 66, reading "(Boyum." should read --(Boyum, --.

Column 5, line 68, reading "(Suppl. 97)" should read -- (Suppl. 97): --.

UNITED STATES PATENT AND TRADEMARK OFFICE
CERTIFICATE OF CORRECTION

PATENT NO. : 4,971,997

DATED : Nov. 20, 1990

INVENTOR(S) : Djuric, et. al.

Page 2 of 4

It is certified that error appears in the above-identified patent and that said Letters Patent is hereby corrected as shown below:

Column 9, Chart A, that portion of the structure reading

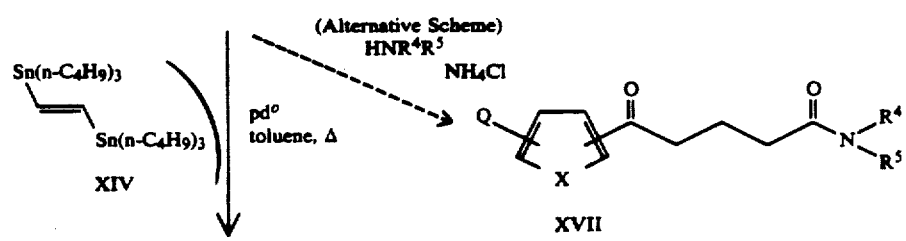

should read

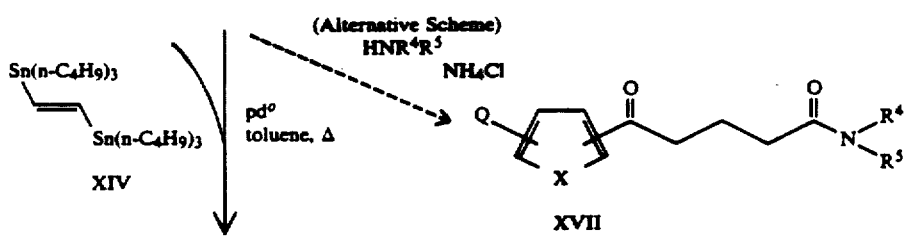

Column 13, line 30, reading "4-pentynoic acid." should read -- 4-pentynoic acid, --.

Column 14, line 59, reading "Org. Chem. 40" should read -- Org. Chem., 40 --.

UNITED STATES PATENT AND TRADEMARK OFFICE
CERTIFICATE OF CORRECTION

PATENT NO. : 4,971,997

DATED : Nov. 20, 1990

INVENTOR(S) : Djuric, et. al.

It is certified that error appears in the above-identified patent and that said Letters Patent is hereby corrected as shown below:

Column 20, line 5, reading "1.28(br. s, 10H); ;0.89" should read -- 1.28(br. s, 10H); 0.89 --.

Column 24, line 55 reading " " should read -- methyl 5-iodo-6-oxo-2-thiophenepentanoate --.

Column 25, line 16, reading " " should read -- methyl 5-(2-bromo-E-ethenyl)-6-oxo-2-thiophenepentanoate --.

Column 25, line 46, reading " " should read -- methyl 5(5-hydroxy 1E,3E-tridecadienyl-6-oxo-2-thiophenepentanoate --.

Column 26, line 6, reading " " should read -- methyl-6- hydroxy-1E,3E-tridecadienyl)-2-thiophenepentanoate --.

Column 26, line 41, reading " " should read -- 3-decynoyl chloride --.

Column 27, line 4, reading " " should read -- 3-decenoyl chloride --.

Column 27, line 34, reading " " should read -- 5-(hydroxy-1E,-3E-tridecadienyl)-6-oxo-2-thiophene-pentanoic acid, lithium salt --.

Column 27, line 55, reading " " should read -- 5-(hydroxy-1E,-3E-tridecadienyl)-6-oxo2-thiophene pentanoic acid, lithium salt --.

Column 28, line 2, reading " " should read -- 2-(5-hydroxy-1E,-3E-tridecadienyl)-6-oxobenzenepentanoic acid, lithium salt --.

UNITED STATES PATENT AND TRADEMARK OFFICE
CERTIFICATE OF CORRECTION

PATENT NO. : 4,971,997

DATED : Nov. 20, 1990

INVENTOR(S) : Djuric, et. al.

It is certified that error appears in the above-identified patent and that said Letters Patent is hereby corrected as shown below:

Column 28, line 34, reading "1-6 carbon atoms." should read -- 1-6 carbon atoms and m is an integer from 0-4. --

Column 28, line 55, reading "1-6 carbon atoms." should read -- 1-6 carbon atoms and m is an integer from 0-4. --.

Signed and Sealed this

Twenty-fourth Day of November, 1992

Attest:

DOUGLAS B. COMER

*Attesting Officer*  *Acting Commissioner of Patents and Trademarks*